US012558385B2

(12) United States Patent
Jeppsson

(10) Patent No.: US 12,558,385 B2
(45) Date of Patent: Feb. 24, 2026

(54) *LACTOBACILLUS PLANTARUM* COMPOSITIONS AND USES THEREOF

(71) Applicant: Probi AB, Lund (SE)

(72) Inventor: Bengt Jeppsson, Lund (SE)

(73) Assignee: Probi AB, Lund (SE)

( * ) Notice: Subject to any disclaimer, the term of this patent is extended or adjusted under 35 U.S.C. 154(b) by 449 days.

(21) Appl. No.: 17/252,854

(22) PCT Filed: Jun. 13, 2019

(86) PCT No.: PCT/EP2019/065590
§ 371 (c)(1),
(2) Date: Dec. 16, 2020

(87) PCT Pub. No.: WO2019/243169
PCT Pub. Date: Dec. 26, 2019

(65) Prior Publication Data
US 2021/0154248 A1      May 27, 2021

(30) Foreign Application Priority Data
Jun. 18, 2018      (WO) ................. PCT/EP2018/066154

(51) Int. Cl.
| | |
|---|---|
| *A61K 35/747* | (2015.01) |
| *A23C 9/123* | (2006.01) |
| *A23L 33/00* | (2016.01) |
| *A23L 33/135* | (2016.01) |
| *A61K 9/20* | (2006.01) |
| *A61K 9/48* | (2006.01) |
| *A61K 35/00* | (2006.01) |
| *A61P 29/00* | (2006.01) |

(52) U.S. Cl.
CPC .......... *A61K 35/747* (2013.01); *A23C 9/1234* (2013.01); *A23L 33/135* (2016.08); *A23L 33/40* (2016.08); *A61K 9/2013* (2013.01); *A61K 9/2018* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61P 29/00* (2018.01); *A23V 2002/00* (2013.01); *A23V 2400/169* (2023.08); *A61K 2035/115* (2013.01)

(58) Field of Classification Search
CPC ................ A61K 35/747; A61K 9/2013; A61K 9/2018; A61K 9/2027; A61K 9/2054; A61K 9/2059; A61K 9/4858; A61K 9/4866; A61K 2035/115; A23C 9/1234; A23L 33/135; A23L 33/40; A61P 29/00; A23V 2002/00; A23Y 2220/67; C12N 1/20; C12R 2001/25
See application file for complete search history.

(56) References Cited

U.S. PATENT DOCUMENTS

| | | | |
|---|---|---|---|
| 8,007,777 B2 | 8/2011 | Borek et al. | |
| 8,540,980 B2 | 9/2013 | London et al. | |
| 8,936,783 B2 * | 1/2015 | Alenfall ................. | A21D 13/40 424/234.1 |
| 10,893,695 B2 * | 1/2021 | Fischer ..................... | A61P 1/02 |
| 2009/0208469 A1 | 8/2009 | Alenfall et al. | |
| 2010/0280132 A1 | 11/2010 | Berggren et al. | |

FOREIGN PATENT DOCUMENTS

| | | |
|---|---|---|
| CA | 3011322 A1 | 7/2017 |
| CN | 1798831 A | 7/2006 |
| CN | 101325960 A | 12/2008 |
| CN | 102210717 A | 10/2011 |
| CN | 102448331 A | 5/2012 |
| JP | 2009-511471 A | 3/2009 |
| WO | 2003/026687 A1 | 4/2003 |
| WO | 2004/087893 A1 | 10/2004 |
| WO | 2007/040446 A1 | 4/2007 |
| WO | 2010/132017 A1 | 11/2010 |
| WO | 2014/163568 A1 | 10/2014 |
| WO | 2016/003870 A1 | 1/2016 |
| WO | 2017/060477 A1 | 4/2017 |
| WO | 2017/125446 A1 | 7/2017 |
| WO | 2018/224509 A1 | 12/2018 |
| WO | 2019/242839 A1 | 12/2019 |

OTHER PUBLICATIONS

Pejcic et al. (C-reactive protein as a systemic marker of inflammation in periodontitis, Eur J Clin Microbiol Infect Dis (2011) 30:407-414). (Year: 2011).*
Koothirezhi et al. (Postmenopausal Syndrome, StatPearls [Internet]. Treasure Island (FL): StatPearls Publishing; Jan. 2023, PMID: 32809675) (Year: 2023).*
Kasperska-Zajac et al. (Plasma IL-6 concentration correlates with clinical disease activity and serum C-reactive protein concentration in chronic urticaria patients, Clinical & Experimental Allergy, 41, 1386-1391, 2011) (Year: 2011).*
McNaught et al. (A prospective randomised trial of probiotics in critically ill patients, Clinical Nutrition (2005) 24, 211-219) (Year: 2005).*
Acevedo et al., Fecal Calprotectin: A Comparison of Two Commercial Enzymoimmunoassays and Study of Fecal Extract Stability at Room Temperature. J Clin Med Res. May 2018; 10(5):396-404.
Adawi et al., Modulation of the Colonic Bacterial Flora Affects Differently Bacterial Translocation and Liver Injury in an Acute Liver Injury Model. Microbial Ecology in Health and Disease. 1999;11:47-54.
Amsen et al., Approaches to determine expression of inflammatory cytokines. Methods Mol Biol. 2009;511:107-42.

(Continued)

*Primary Examiner* — Louise W Humphrey
*Assistant Examiner* — Alexander M Duryee
(74) *Attorney, Agent, or Firm* — McCarter & English, LLP; Yu Lu

(57) ABSTRACT

The invention relates to methods for treating and/or preventing age-related systemic inflammation by administering to a human in need thereof, at least one probiotic strain of *Lactobacillus plantarum*. Also described are compositions, dosages and probiotic strains suitable for the methods. The probiotic strain has beneficial effects on age-related systemic inflammation in otherwise healthy elderly individuals.

14 Claims, 1 Drawing Sheet

(56)                    References Cited

OTHER PUBLICATIONS

Axling et al., Green tea powder and Lactobacillus plantarum affect gut microbiota, lipid metabolism and inflammation in high-fat fed C57BL/6J mice. Nutr Metab (Lond). Nov. 26, 2012;9(1):105. 18 pages.

Bartlett et al., The age-related increase in low-grade systemic inflammation (Inflammaging) is not driven by cytomegalovirus infection. Aging Cell. Oct. 2012;11(5):912-5.

Castillo et al., Cytokine measurement using cytometric bead arrays. Methods Mol Biol. 2012;845:425-34.

Chiswick et al., Detection and quantification of cytokines and other biomarkers. Methods Mol Biol. 2012;844:15-30.

ClinicalTrials.gov, NCT02342496, Probiotics Against Low Grade Inflammation and Increased Intestinal Permeability in the Elderly. 3 pages, Apr. 9, 2018.

Dominici et al., Measurement of C-reactive protein: two high sensitivity methods compared. J Clin Lab Anal. 2004;18(5):280-4.

Franceschi et al., Inflamm-aging. An evolutionary perspective on immunosenescence. Ann N Y Acad Sci. Jun. 2000;908:244-54.

Gray, Gut bacteria control age-related inflammation: Mouse data. NUTRA ingredients.com. Retrieved online at: http://www.nutraingredients.com/content/view/print/1395370, 2 pages, Apr. 19, 2017.

Hill et al., The International Scientific Association for Probiotics and Prebiotics consensus statement on the scope and appropriate use of the term probiotic. Nat Rev Gastroenterol Hepatol. Aug. 2014;11(8):506-14.

Jacobsen et al., Screening of probiotic activities of forty-seven strains of Lactobacillus spp. by in vitro techniques and evaluation of the colonization ability of five selected strains in humans. Appl Environ Microbiol. Nov. 1999;65(11):4949-56.

Jeong et al., Orally administrated Lactobacillus pentosus var. plantarum C29 ameliorates age-dependent colitis by inhibiting the nuclear factor-kappa B signaling pathway via the regulation of lipopolysaccharide production by gut microbiota. PLoS One. Feb. 17, 2015;10(2):e0116533. 16 pages.

Johansson et al., Administration of different Lactobacillus strains in fermented oatmeal soup: in vivo colonization of human intestinal mucosa and effect on the indigenous flora. Appl Environ Microbiol. Jan. 1993;59(1):15-20.

Klarin et al., Use of the probiotic Lactobacillus plantarum 299 to reduce pathogenic bacteria in the oropharynx of intubated patients: a randomised controlled open pilot study. Crit Care. 2008;12(6):R136, 8 pages.

Lash et al., Comparison of three multiplex cytokine analysis systems: Luminex, SearchLight and FAST Quant. J Immunol Methods. Feb. 20, 2006;309(1-2):205-8.

Mao et al., Comparison of the Effects of Different Strains of Lactobacillus in Reducing Bacterial Translocation on Methotrexate-Induced Enterocolitis in Rats. Dig Surg. 1997;14:284-291.

Olah et al., Randomized clinical trial of specific lactobacillus and fibre supplement to early enteral nutrition in patients with acute pancreatitis. Br J Surg. Sep. 2002;89(9):1103-7.

Olsson, Bakterier som boostar hälsan. Hälsa magazine. 2018;5:42-46.

Pathmakanthan et al., Lactobacillus plantarum 299: beneficial in vitro immunomodulation in cells extracted from inflamed human colon. J Gastroenterol Hepatol. Feb. 2004;19(2):166-73.

Pearson et al., Markers of inflammation and cardiovascular disease: application to clinical and public health practice: A statement for healthcare professionals from the Centers for Disease Control and Prevention and the American Heart Association. Circulation. Jan. 28, 2003;107(3):499-511.

Prior, Perimenopause. CeMCOR, retrieved online at: http://cemcor.ca/help_yourself/perimenopause. 4 pages, Feb. 25, 2013.

Probi® Select Senior. Retrieved online at: www.probi.com. 2 pages, retreived online: May 15, 2018.

Rayes et al., Early enteral supply of fiber and Lactobacilli versus conventional nutrition: a controlled trial in patients with major abdominal surgery. Nutrition. Jul.-Aug. 2002;18(7-8):609-15.

Rayes et al., Early enteral supply of lactobacillus and fiber versus selective bowel decontamination: a controlled trial in liver transplant recipients. Transplantation. Jul. 15, 2002;74(1):123-7.

Rayes et al., Einfluss von Probiotika und Ballaststoffen auf die Inzidenz bakterieller Infektionen nach viszeralchirurgischen Eingriffen—Ergebnisse einer prospektiven Studie [Influence of probiotics and fibre on the incidence of bacterial infections following major abdominal surgery—results of a prospective trial]. Z Gastroenterol. Oct. 2002;40(10):869-76.

Redmond et al., Cytokine Cell Culture Assays. Animal Cell Culture Technique. M. Clynes (Ed.). Springer-Verlag, Berlin. Chapter 28, pp. 521-541, (1998).

Shine et al., Solid phase radioimmunoassays for human C-reactive protein. Clin Chim Acta. Nov. 25, 1981;117(1):13-23.

Tamassia et al., Fast and accurate quantitative analysis of cytokine gene expression in human neutrophils by reverse transcription real-time PCR. Methods Mol Biol. 2007;412:455-71.

The North American Menopause Society, Menopause 101: A primer for the perimenopausal. Retrieved online at: www.menopause.org/for women/menopauseflashes/menopause 101 a primer-for-the-perimenopausal. 2 pages, (2021).

Thevaranjan et al., Age-Associated Microbial Dysbiosis Promotes Intestinal Permeability, Systemic Inflammation, and Macrophage Dysfunction. Cell Host Microbe. Apr. 12, 2017;21(4):455-466.e4.

Vilahur et al., Lactobacillus plantarum CECT 7315/7316 intake modulates the acute and chronic innate inflammatory response. Eur J Nutr. Oct. 2015;54(7):1161-71.

White et al., The probiotic bacterium Lactobacillus plantarum species 299 reduces intestinal permeability in experimental biliary obstruction. Lett Appl Microbiol. Jan. 2006;42(1):19-23.

International Search Report and Written Opinion for Application No. PCT/EP2019/065590, dated Sep. 23, 2019, 11 pages.

* cited by examiner

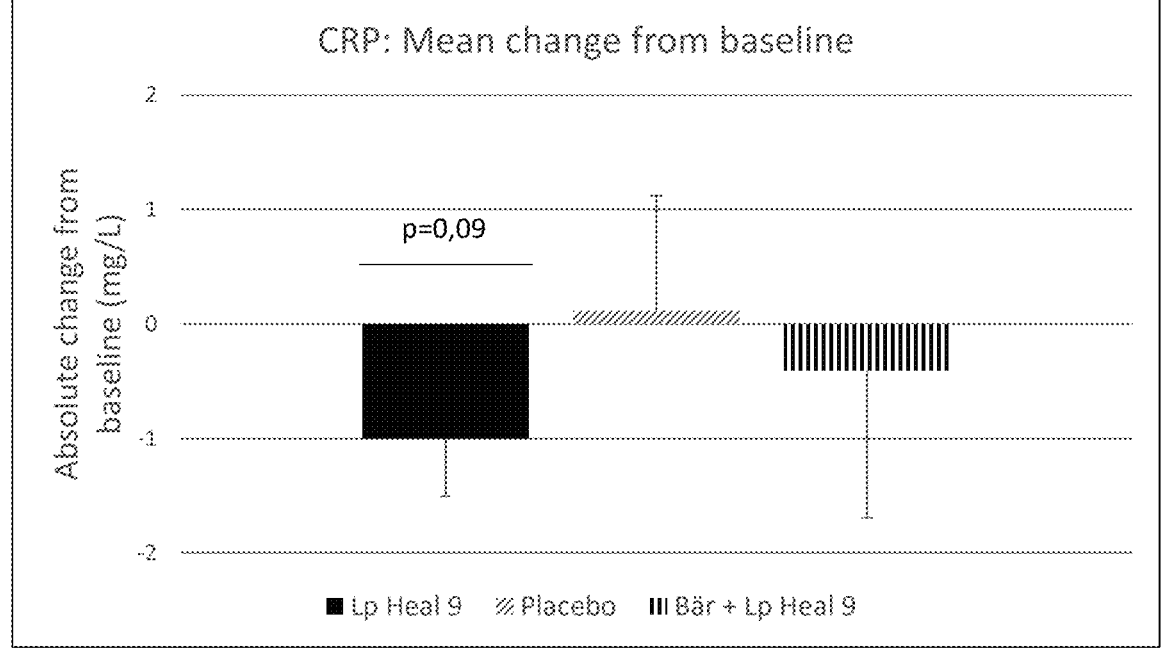

LACTOBACILLUS PLANTARUM COMPOSITIONS AND USES THEREOF

CROSS-REFERENCE TO RELATED APPLICATIONS

This application is a U.S. national stage filing, under 35 U.S.C. § 371(c), of International Application No. PCT/EP2019/065590, filed on Jun. 13, 2019, which claims priority to International Application No. PCT/EP2018/066154, filed on Jun. 18, 2018. The entire contents of each of the aforementioned applications are incorporated herein by reference.

TECHNICAL FIELD OF HE INVENTION

The present invention relates to at least one probiotic strain of *Lactobacillus plantarum* for use in the treatment and/or prevention of age-related systemic inflammation in a human. The present invention also relates to pharmaceutical compositions thereof. Further, the present invention relates to methods and uses of the at least one probiotic strain of *Lactobacillus plantarum* and/or of pharmaceutical compositions thereof.

BACKGROUND OF THE INVENTION

The human ageing process involves almost all organs throughout the body, with a gradual decline in function. Ageing is associated with higher levels of low-grade systemic inflammation that does not have a direct impact on the everyday life of the elderly but could increase the risk for other diseases, such as cardiovascular disease, insulin resistance and diabetes, osteoporosis, decreased cognitive function and dementia, and various cancers, and results in increased mortality. Age-related low-grade systemic inflammation, also known as 'inflamm-aging' (Franceschi et al, 2000, *Ann N Y Acad Sci* 908:244-254) is typically characterised by raised levels of C-reactive protein (CRP) and pro-inflammatory cytokines, such as interleukin 6 (IL-6) and tumour necrosis factor alpha (TNFα), and reduced levels of anti-inflammatory cytokines, such as interleukin-10 (IL-10) (Bartlett et al, 2012, *Aging Cell* 11:912-915).

The causes of the above changes are not known, nor is an effective treatment or prevention of age-related systemic inflammation known in the art.

Surprisingly, the inventor has shown that administration of a specific species of probiotic bacteria, *Lactobacillus plantarum*, has remarkable effects on age-related systemic inflammation in otherwise healthy elderly individuals.

DESCRIPTION OF THE INVENTION

According to a first aspect, the invention provides at least one probiotic strain of *Lactobacillus plantarum* for use in the treatment and/or prevention of age-related systemic inflammation in a human.
Age-Related Systemic Inflammation By "systemic inflammation" we include the meaning of systemic inflammation, which is generally the result of the release of pro-inflammatory cytokines from immune-related cells and the activation of the innate immune system. We particularly include the meaning of chronic systemic inflammation, which is typically when activation of the innate immune system persists beyond an initial acute phase and becomes 'chronic'.

By "age-related systemic inflammation" we include the meaning that the systemic inflammation is chronic and associated with the ageing process. Hence, age-related systemic inflammation does not include acute systemic inflammation caused by a single trauma (e.g. snake bite, burns, heart attack, or infections such as pneumonia). Typically, age-related systemic inflammation may be present in otherwise healthy individuals, particularly in the elderly.

Hence, systemic inflammation is indicated by markers in the blood and is different fro local inflammation which occurs in the tissues/organs of the body.

We believe that age-related systemic inflammation can contribute to the development or progression of, and/or be a risk factor for, other conditions, including cardiovascular disease, insulin resistance and diabetes, osteoporosis, decreased cognitive function and dementia, and various cancers. For example, there is now scientific acceptance that serum levels of CRP above 3 mg/L are associated with an increased risk of cardiovascular disease.

Generally, systemic inflammation can be categorised as 'low-grade systemic inflammation' when markers of inflammation, primarily CRP, cannot be attributed to viral or bacterial infection.

In the below examples, serum CRP levels of 2-10 mg/L were used to define the low grade systemic inflammation group of patients to be treated according to the invention.
Treatment and Prevention By "use in the treatment and/or prevention" we include the meaning of a use which gives rise to an effect in a subject of preventing, delaying, protecting against, reducing the severity of and/or removing, one or more symptoms and/or other markers associated with a disease or condition.

By "treat", "treatment" or "treating" we include the meaning that the event or condition being treated is ameliorated, reduced in severity, removed, blocked from occurring further, protected against occurring further, delayed and/or made to cease. Such treatment typically takes place after the event (or the same kind of event) has occurred or the condition is manifest. It will also be appreciated that such terms may include the meaning that an event or condition is maintained in the current state without becoming worse or developing further.

By "prevent", "prevention" or "preventing" we include the meaning that the event or condition being prevented is protected against, delayed, reduced (e.g. reduced in severity), blocked from occurring, or made to cease. Such prevention typically takes place before the event occurs or the condition is manifest, but it will be appreciated that it can also mean to prevent further occurrence of the same kind of event. It will also be appreciated that such terms may include the meaning that an event or condition is maintained in the current state without becoming worse or developing further.

For example, a symptom of age-related systemic inflammation following administration of the at least one probiotic strain of *Lactobacillus plantarum* according to the first aspect of the invention may be improved by at least 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or at least 99% compared to without administration of the at least one probiotic strain of *Lactobacillus plantarum*.

For example, the treatment and/or prevention of age-related systemic inflammation may involve reducing and/or preventing an increase in the level of C-reactive protein (CRP) and/or may involve reducing and/or preventing an increase in the level of calprotectin.

C-Reactive Protein and Calprotectin

C-reactive protein (CRP) is an acute-phase protein produced by the liver that increases following interleukin-6 secretion by macrophages and T cells. Hence the level of CRP in blood plasma rises in response to the presence of inflammation in the body. The physiological role of CRP is to bind to lysophosphatidylcholine expressed on the surface of dead or dying cells (and some types of bacteria) in order to activate the complement system via C1 q.

The level of CRP can measured by any suitable method known in the art. CRP is typically measured by a routine blood test to determine the concentration of CRP in blood plasma, for example using antibodies specific to CRP. Examples of tests to measure CRP include those described in Dominici et al (2004) *J Clin Lab Anal* 18(5):280-284, immunochromatographic assays and ELISA tests, e.g. the Eurolyser CRP assay using photometric kinetic determination of the reaction between plasma CRP and an immobilised anti-CRP antibody. A high-sensitivity C-reactive protein (hs-CRP) assay may also be used (Pearson et al, 2003, *Circulation* 107(3):499-511), as is common in determining risk for heart disease.

Healthy adults typically have a serum CRP level of up to 10 mg/L (Shine et al, 1981, *Clin Chim Acta* 117(1):13-23), and in one study 90% of 468 healthy adult volunteers had a serum CRP level of less than 3 mg/L (Shine et al, 1981, *Clin Chim Acta* 117(1):13-23). A level of CRP higher than 10 mg/L, often much higher, is typically a sign of serious infection, trauma or chronic disease.

Individuals with age-related systemic inflammation typically have a serum CRP level of 2 to 10 mg/L, for example from 2 to 10 mg/L, from 3 to 10 mg/L, from 4 to 10 mg/L, from 5 to 10 mg/L, from 6 to 10 mg/L, from 7 to 10 mg/L, from 8 to 10 mg/L, from 9 to 10 mg/L, from 2 to 3 mg/L, from 2 to 4 mg/L, from 2 to 5 mg/L, from 2 to 6 mg/L, from 2 to 7 mg/L, from 2 to 8 mg/L or from 2 to 9 mg/L. Individuals with a serum CRP level less than 2 mg/L may be considered as not having systemic inflammation.

Hence, it will be appreciated that the level of in CRP in serum of a subject/patient following administration of the at least one probiotic strain of *Lactobacillus plantarum* according to the first aspect of the invention may be improved by at least 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or at least 99% compared to the level of CRP without administration of the at least one probiotic strain of *Lactobacillus plantarum*.

Calprotectin is a protein released into the intestinal lumen by neutrophils in response to inflammation of the gastrointestinal tract. Neutrophils migrate to the intestinal mucosa during intestinal inflammation. The level of calprotectin in faecal samples rises in response to the presence of inflammation in the gastrointestinal tract, including in individuals with inflammatory bowel disease (IBD) (e.g. ulcerative colitis or Crohn's disease) or some bacterial infections of the gastrointestinal tract. Specifically, calprotectin can be used to help distinguish between inflammatory bowel conditions (e.g. IBD) and non-inflammatory bowel conditions (e.g. irritable bowel syndrome).

The level of calprotectin can be measured by any suitable method known in the art. Calprotectin is typically measured in faecal samples to determine the concentration of calprotectin, for example using antibodies specific to calprotectin. Examples of tests to measure calprotectin include those described in Acevedo et al (2018) *J Clin Med Res* 10(5): 396-404, immunochromatographic assays and ELISA tests, e.g. BÜHLMANN fCAL® ELISA (Bühlmann), Quantum Blue® fCAL (Bühlmann) or CalFast® (Eurospital).

A level of faecal calprotectin up to 110 µg/g faeces is typically considered normal. A level of faecal calprotectin between 110 and 1800 µg/g faeces is typically considered to be 'raised' and indicative of inflammation. However, a mildly raised level of faecal calprotectin over 110 µg/g faeces may still be normal.

Hence, it will be appreciated that the level of calprotectin following administration of the at least one probiotic strain of *Lactobacillus plantarum* according to the first aspect of the invention may be improved by at least 0.5%, 1%, 2%, 3%, 4%, 5%, 6%, 7%©, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or at least 99% compared to the level of calprotectin without administration of the at least one probiotic strain of *Lactobacillus plantarum*.

Probiotic Strains

Probiotic bacteria are defined as "live microorganisms that, when administered in adequate amounts, confer a health benefit on the host" (Hill et al, Nat Rev Gastroenterol Hepatol, 2014, 11(8):506-514). Bacteria of the genera *Lactobacillus* and *Bifidobacterium* are the most frequently used bacteria in probiotic products. These bacteria are generally safe, as are probiotic products based on these organisms. For a bacterium to fulfil the definition of a probiotic it typically has to be able to survive in and colonise the intestines, survive the processes of production and storage, and have evidence that it has positive effects on consumer health.

The at least one probiotic strain of *Lactobacillus plantarum* according to the first aspect of the invention may be any probiotic strain of *Lactobacillus plantarum*.

Preferably, the at least one probiotic strain of *Lactobacillus plantarum* according to the first aspect of the invention is chosen from *Lactobacillus plantarum* 299 (DSM 6595), *Lactobacillus plantarum* 299v (DSM 9843), *Lactobacillus plantarum* HEAL 9 (DSM 15312), *Lactobacillus plantarum* HEAL 19 (DSM 15313), *Lactobacillus plantarum* HEAL 99 (DSM 15316) or *Lactobacillus plantarum* GOS42 (DSM 32131).

Most preferably, the at least one probiotic strain of *Lactobacillus plantarum* according to the first aspect of the invention is *Lactobacillus plantarum* HEAL 9 (DSM 15312).

*Lactobacillus plantarum* 299 (DSM 6595) was deposited on 2 Jul. 1991 at DSM-DEUTSCHE SAMMLUNG VON MIKROORGANISMEN UND ZELLKULTUREN GmbH in the name of Probi.

*Lactobacillus plantarum* 299v (DSM 9843) was deposited on 16 Mar. 1995 at DSM-DEUTSCHE SAMMLUNG VON MIKROORGANISMEN UND ZELLKULTUREN GmbH, Mascheroder Weg 1 b, D-38124 Braunschweig, Germany, by Probi AB.

*Lactobacillus plantarum* HEAL 9, DSM 15312, *Lactobacillus plantarum* HEAL 19, DSM 15313, and *Lactobacillus plantarum* HEAL 99, DSM 15316 were deposited on 27 Nov. 2002 at DSMZ-DEUTSCHE SAMMLUNG VON MIKROORGANISMEN UND ZELLKULTUREN GmbH, Mascheroder Weg 1 b, D-38124 Braunschweig, Germany, by Probi AB.

*Lactobacillus plantarum* GOS42 (DSM 32131) was deposited on 2 Sep. 2015 at Leibniz Institute DSMZ-German Collection of Microorganisms and Cell Cultures, Inhoffenstr. 7 B, D-38124 Braunschweig, Germany by Probi AB.

The compositions of the present invention may comprise the specified one or more probiotic strains of *Lactobacillus plantarum*, but preferably they consist of the specified one or more probiotic strains without another effective amount of any other probiotic strain of *Lactobacillus* and/or *Bifido-bacterium* or other micro-organisms.

The probiotic strains according to the first aspect of the invention may be viable, attenuated, inactivated, or dead. Preferably, the probiotic strains are viable. For example, preferably the probiotic strains are freeze-dried.

Patient Group

The at least one probiotic strain of *Lactobacillus plantarum* according to the first aspect of the invention must be suitable for use in a human. For example, the human may be aged more than 40, 45, 50, 55, 60, 65, 70, 75, 80, 85 or 90 years.

Preferably, the at least one probiotic strain of *Lactobacillus plantarum* is for use in elderly people, for example a human aged more than 70, 75, 80, 85 or 90 years.

The at least one probiotic strain of *Lactobacillus plantarum* may be for use in a man.

The at least one probiotic strain of *Lactobacillus plantarum* may be for use in a woman, including a post-menopausal woman. The at least one probiotic strain of *Lactobacillus plantarum* may be for use in a woman from the onset of menopause. The at least one probiotic strain of *Lactobacillus plantarum* may be for use in a woman up to 10 years after the start of menopause, for example, up to 6 years, 7 years, 8 years, 9 years or 10 years after the start of menopause.

Menopause is the time in most women's lives when menstrual periods stop permanently, and they are no longer able to bear children. Menopause typically occurs between 49 and 52 years of age. Medical professionals often define menopause as having occurred when a woman has not had any vaginal bleeding for a year. Hence, the date of menopause itself is typically determined retroactively, once 12 months have passed after the last appearance of menstrual blood.

Compositions

The at least one probiotic strain according to the first aspect of the invention may be present in a composition comprising at least one suitable carrier. For example, the carrier may be a diluent or excipient. The composition may be as a solid or liquid formulation, and hence the at least one carrier may be a solid or a liquid, or may comprise both at least one solid component and at least one liquid component.

Examples of a suitable liquid carrier include water, milk, coconut water, fruit drinks and juices, milk substitutes (soya drink, oat drink, nut and other plant-based drinks), sparkling beverages, glycerin, propylene glycol and other aqueous solvents.

Examples of a suitable solid carrier or excipient include maltodextrin, inulin, a cellulose such as microcrystalline cellulose (MCC), hydroxypropylmethylcellulose (HPMC) or hydroxy-propylcellulose (HPC), sugar alcohols, high molecular weight polyethylene glycols, lactose, sodium citrate, calcium carbonate, dibasic calcium phosphate and glycine, disintegrants such as starch (preferably corn, potato, tapioca or other vegetable starch), sodium starch glycollate, croscarmellose sodium and certain complex silicates, and granulation binders such as polyvinylpyrrolidone, sucrose, gelatin and acacia. Additionally, lubricating agents such as magnesium stearate, stearic acid, glyceryl behenate and talc may be included.

In an embodiment according to the first aspect of the invention, the carrier may be selected from a pharmaceutically acceptable carrier, a pharmaceutically acceptable excipient, a diluent and a food.

Examples of suitable pharmaceutically acceptable carriers, excipients and diluents include those well known to a skilled person in the art, for example those given in Remington: The Science and Practice of Pharmacy, 19th ed., vol. 1 & 2 (ed. Gennaro, 1995, Mack Publishing Company).

By "food" we include any substance for consumption to provide nutritional benefit or support for an organism. Examples of suitable food carriers include beverages (e.g. juices), dairy products (e.g. yoghurts, cheese, ice creams, infant formula and spreads such as margarine), dairy-alternative products (e.g. soy, nut or other plant-based drinks, yoghurts and spreads), cereal-based products (e.g. breads, biscuits, breakfast cereals, pasta and dry food bars such as health bars), and baby food (e.g. pureed fruit and/or vegetable).

The composition according to the first aspect of the invention may be a dry, non-fermented composition, a fermented composition, or a dry, fermented composition. Fermentation in this context particularly includes lactic acid fermentation by lactic acid bacteria in anaerobic conditions. In the case of a dry, non-fermented composition, substantially no fermentation takes place before ingestion by a subject, and so fermentation only takes place in the gastrointestinal tract after ingestion of the composition by a subject.

Hence, in some embodiments according to the first aspect of the invention, the composition is in the form of a food wherein the food is a cereal-based product, a dairy product, a juice drink, or a fermented food.

Examples of fermented foods include fermented milk products (such as yoghurt, kefir or lassi), fermented dairy-free milk alternatives (such as coconut milk kefir), fermented cereal-based products (such as oats, oatmeal, maize, sorghum, wheat), fermented vegetables (such as sauerkraut, kimchi, or pickles), fermented legumes or soybeans (such as natto or tempeh) and fermented tea (such as kombucha).

In some embodiments according to the first aspect of the invention, the at least one probiotic strain is present in a composition that is not naturally occurring, e.g. the composition comprises more than the probiotic strain(s) and water.

In use, the at least one probiotic strain or the composition comprising the at least one probiotic strain according to the first aspect of the invention may be mixed with a liquid or solid carrier before administration to a mammal. For example, a subject may mix the at least one probiotic strain or the composition thereof with a carrier comprising one or more liquids chosen from water, milk, coconut water, fruit drinks and juices, milk substitutes (soya drink, oat drink, nut and other plant-based drinks), sparkling beverages or some other aqueous solvent or drink prior to intake. Similarly, the at least one probiotic strain or the composition thereof may be mixed with a carrier consisting of one or more foods. Suitable food carriers include oatmeal carrier, barley carrier, fermented or non-fermented dairy products such as yoghurts, ice creams, milkshakes, fruit juices, beverages, soups, breads, biscuits, pasta, breakfast cereals, dry food bars including health bars, plant-based foods such as soy products, spreads, baby food, infant nutrition, infant formula, or breast milk replacements from birth.

Preferably, the formulation is a unit dosage containing a daily dose or unit, daily sub-dose or an appropriate fraction thereof, of the composition comprising the probiotic strains.

The composition according to the first aspect of the invention may be a dietary supplement. By "dietary supplement" we include the meaning of a manufactured product intended to supplement the diet when taken by mouth, e.g. as a pill, capsule, tablet, or liquid. Dietary supplements may contain substances that are essential to life and/or those that have not been confirmed as being essential to life but may have a beneficial biological effect. When the composition according to the first aspect of the invention is in the form of a dietary supplement the carrier(s) to be added include those well known to a skilled person in the art, for example those given in Remington: The Science and Practice of Pharmacy, 19$^{th}$ ed, vol. 1 & 2 (ed. Gennaro, 1995, Mack Publishing Company). Any other ingredients that are normally used in dietary supplements are known to a skilled person and may also be added conventionally together with the at least one probiotic strain.

The composition according to the first aspect of the invention may be provided in the form of a solution, suspension, emulsion, tablet, granule, powder, capsule, lozenge, chewing gum, or suppository.

In an embodiment according to the first aspect of the invention, the at least one probiotic strain is present (e.g. in a composition) in an amount from about $1\times10^8$ to about $1\times10^{14}$ CFU/dose, preferably from about $1\times10^8$ to about $1\times10^{12}$ CFU/dose, more preferably from about $1\times10^9$ to about $1\times10^{11}$ CFU/dose, and most preferably about $1\times10^{10}$ CFU/dose. If the at least one probiotic strain consists of more than one probiotic strain, such amounts represent the total CFU/dose of the combination of probiotic strains. For example, the at least one probiotic strain may be present in an amount from about $1\times10^6$, $1\times10^7$, $1\times10^8$, $1\times10^9$, $1\times10^{10}$, $1\times10^{11}$, $1\times10^{12}$ or about $1\times10^{13}$ CFU/dose. The at least one probiotic strain may be present in an amount to about $1\times10^{14}$, $1\times10^{13}$, $1\times10^{12}$, $1\times10^{11}$, $1\times10^{10}$, $1\times10^9$, $1\times10^8$ or about $1\times10^7$ CFU/dose. The at least one probiotic strain according to the first aspect of the invention may also be used alone in water or any other aqueous vehicle in which the at least one probiotic strain is added or mixed before ingestion.

The composition according to the first aspect of the invention can be administered orally, buccally or sublingually in the form of tablets, capsules, powders, ovules, elixirs, solutions or suspensions, which may contain flavouring or colouring agents, for immediate-, delayed- or controlled-release applications. The composition may be administered in the form of a powdered composition such as a fast-melt microbial composition, for example those described in WO 2017/060477 and UK Patent Application 1708932.7, the entire contents of which are incorporated herein by reference.

The composition according to the first aspect of the invention may be formulated as a controlled-release solid dosage form, for example any of those described in WO 03/026687 and U.S. Pat. Nos. 8,007,777 and 8,540,980, the entire contents of which are incorporated herein by reference. The composition may be formulated as a layered dosage form, for example any of those described in WO 2016/003870, the entire contents of which are incorporated herein by reference.

A tablet may be made by compression or moulding, optionally with one or more accessory ingredients. Compressed tablets may be prepared by compressing in a suitable machine the at least one probiotic strain (e.g. freeze-dried) in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

Pharmaceutical Compositions

A second aspect of the invention provides a pharmaceutical composition comprising the at least one probiotic strain according to the first aspect of the invention, and one or more pharmaceutically acceptable excipients, for use in the treatment and/or prevention of age-related systemic inflammation in a human.

The pharmaceutical composition according to the second aspect of the invention may be a composition as described above in respect of the first aspect of the invention. The term "pharmaceutically acceptable" includes that the one or more excipients must not be deleterious to the recipients thereof and must be compatible with the at least one probiotic strain according to the first aspect of the invention. Examples of such pharmaceutically acceptable excipients are well known in the art and include those described above in respect of the first aspect of the invention, for example those described in Remington: The Science and Practice of Pharmacy, 19th ed., vol. 1 & 2 (ed. Gennaro, 1995, Mack Publishing Company).

For example, the pharmaceutical composition may be formulated as a controlled-release solid dosage form, e.g. any of those described in WO 03/026687 and U.S. Pat. Nos. 8,007,777 and 8,540,980, or the pharmaceutical composition may be formulated as a layered dosage form, e.g. any of those described in WO 2016/003870.

The one or more pharmaceutically acceptable excipients may be water or saline which will be sterile and pyrogen free.

Preferably, the pharmaceutical composition according to the second aspect of the invention may be administered by any conventional method including oral and tube feeding. Administration may consist of a single dose or a plurality of doses over a period of time.

Methods of Treatment

A third aspect of the invention provides a method for treating and/or preventing age-related systemic inflammation in a human, comprising administering to a human in need thereof a therapeutically effective amount of the at least one probiotic strain according the first aspect of the invention or the pharmaceutical composition according to the second aspect of the invention.

In particular, the methods according to the third aspect of the invention include those wherein the prevention of age-related systemic inflammation in a human is indicated by reducing serum levels of one or more markers of age-related systemic inflammation compared to not having been administered said probiotic strains.

The methods according to the third aspect of the invention may be carried out on any human defined above in relation to the first aspect of the invention. For example, the human may be aged more than 40, 45, 50, 55, 60, 65, 70, 75, 80, 85 or 90 years.

Preferably, the methods according to the third aspect of the invention are carried out on elderly people, for example a human aged more than 70, 75, 80, 85 or 90 years.

The methods according to the third aspect of the invention may be carried out on a man.

The methods according to the third aspect of the invention may be carried out on a woman, including a post-menopausal woman. The methods according to the third aspect of the invention may be carried out on a woman from the onset of menopause. The methods according to the third aspect of the invention may be carried out on a woman up to 10 years after the start of menopause, for example, up to 6 years, 7 years, 8 years, 9 years or 10 years after the start of menopause.

Preferably, the serum level of CRP is reduced to less than 3 ore preferably less than 2 mg/L.

Administration according to the methods of the third aspect of the invention may include administration orally, buccally or sublingually as described above in relation to the first aspect of the invention.

Administration according to the methods of the third aspect of the invention preferably takes place at least once daily.

Administration according to the methods of the third aspect of the invention may include administration that is repeated for up to one, two, three, four or five weeks, for up to one, two, three, four, five, six, seven, eight, nine, ten, eleven or twelve months, or for more than one, two or three years or longer. Preferably, administration is repeated for at least one week, two weeks, three weeks, more preferably for at least four weeks, one month, two months or three months, and even more preferably for at least six months, nine months or one year.

Administration according to the methods of the third aspect of the invention is preferably of a unit dosage of from about $1\times10^6$ to about $1\times10^{14}$ CFU/unit dose, preferably from about $1\times10^8$ to $1\times10^{12}$ CFU/unit dose, and more preferably from about $1\times10^9$ to about $1\times10^{11}$ CFU/unit dose, and most preferably about $1\times10^{10}$ CFU/unit dose, in accordance with the first aspect of the invention. Administration according to the methods of the third aspect of the invention preferably results in an effective dose of from about $1\times10^6$ to about $1\times10^{14}$ CFU/unit dose, preferably from about $1\times10^8$ to about $1\times10^{12}$ CFU/unit dose, more preferably from about $1\times10^9$ to about $1\times10^{11}$ CFU/unit dose, and most preferably about $1\times10^{10}$ CFU/unit dose. Preferably, each subject is administered one unit dose per day. Hence, administration according to the methods of the third aspect of the invention preferably results in a daily dose of from about $1\times10^6$ to about $1\times10^{14}$ CFU/day, preferably from about $1\times10^8$ to about $1\times10^{12}$ CFU/day, more preferably from about $1\times10^9$ to about $1\times10^{11}$ CFU/day, and most preferably about $1\times10^{10}$ CFU/day.

It will be appreciated that a preferable daily dose may also be achieved by administration of more than one sub-dose, for example, by a twice daily administration of a unit dose comprising half of the preferable daily dose. Hence, the preferred ranges for the effective dose may also represent the preferred daily dosage to be achieved in whatever number of unit doses is practical.

The subject may be instructed to consume the therapeutically effective amount of the at least one probiotic strain according the first aspect of the invention or the pharmaceutical composition according to the second aspect of the invention, in combination with water, another aqueous solvent or a food product, e.g. yoghurt.

Use in Treatment and/or Prevention

A fourth aspect of the invention provides the use of a composition comprising the at least one probiotic strain according to the first aspect of the invention, or the pharmaceutical composition according to the second aspect of the invention, in the treatment and/or prevention of age-related systemic inflammation in a human.

The listing or discussion of an apparently prior-published document in this specification should not necessarily be taken as an acknowledgement that the document is part of the state of the art or is common general knowledge, The invention will now be described in more detail by reference to the following Examples and FIGURE.

BRIEF DESCRIPTION OF THE FIGURES

FIG. 1 shows the mean change in actual/absolute mg/L serum values of C-reactive protein (CRP) levels from baseline, after four weeks of treatment, for each of the three treatment groups.

EXEMPLARY DOSAGE FORMS

In addition to the formulations referenced above (and incorporated herein by reference), the following examples illustrate pharmaceutical formulations according to the invention.

Example A: Tablet

| | |
|---|---|
| Probiotic strain(s) | $1\times10^9$ CFU |
| Lactose | 200 mg |
| Starch | 50 mg |
| Polyvinylpyrrolidone | 5 mg |
| Magnesium stearate | 4 mg |

Tablets are prepared from the foregoing ingredients by wet granulation followed by compression.

Example B: Tablet Formulations

The following formulations A and B are prepared by wet granulation of the ingredients with a solution of povidone, followed by addition of magnesium stearate and compression.

Formulation A

| | | |
|---|---|---|
| (a) Probiotic strain(s) | $1\times10^9$ CFU | $1\times10^9$ CFU |
| (b) Lactose B.P. | 210 mg | 26 mg |
| (c) Povidone B.P. | 15 mg | 9 mg |
| (d) Sodium Starch Glycolate | 20 mg | 12 mg |
| (e) Magnesium Stearate | 5 mg | 3 mg |

Formulation B

| | | |
|---|---|---|
| (a) Probiotic strain(s) | $1\times10^9$ CFU | $1\times10^9$ CFU |
| (b) Lactose | 150 mg | — |
| (c) Avicel PH 101 ® | 60 mg | 26 mg |
| (d) Povidone B.P. | 15 mg | 9 mg |
| (e) Sodium Starch Glycolate | 20 mg | 12 mg |
| (f) Magnesium Stearate | 5 mg | 3 mg |

Formulation C

| | |
|---|---|
| Probiotic strain(s) | $1\times10^9$ CFU |
| Lactose | 200 mg |
| Starch | 50 mg |
| Povidone | 5 mg |
| Magnesium stearate | 4 mg |

The following formulations, D and E, are prepared by direct compression of the admixed ingredients. The lactose used in formulation E is of the direction compression type.

Formulation D

| Probiotic strain(s) | $1 \times 10^9$ CFU |
|---|---|
| Pregelatinised Starch NF15 | 150 mg |

Formulation E

| Probiotic strain(s) | $1 \times 10^9$ CFU |
|---|---|
| Lactose | 150 mg |
| Avicel ® | 100 mg |

Formulation F (Controlled Release Formulation)

The formulation is prepared by wet granulation of the ingredients (below) with a solution of povidone followed by the addition of magnesium stearate and compression.

| (a) Probiotic strain(s) | $1 \times 10^9$ CFU |
|---|---|
| (b) Hydroxypropylmethylcellulose (Methocel K4M Premium) ® | 112 mg |
| (c) Lactose B.P. | 53 mg |
| (d) Povidone B.P.C. | 28 mg |
| (e) Magnesium Stearate | 7 mg |

Release takes place over a period of about 6-8 hours and was complete after 12 hours.

Example C: Capsule Formulations

Formulation A

A capsule formulation is prepared by admixing the ingredients of Formulation D in Example B above and filling into a two-part hard gelatin capsule. Formulation B (infra) is prepared in a similar manner.

Formulation B

| (a) Probiotic strain(s) | $1 \times 10^9$ CFU |
|---|---|
| (b) Lactose B.P. | 143 mg |
| (c) Sodium Starch Glycolate | 25 mg |
| (d) Magnesium Stearate | 2 mg |

Formulation C

| (a) Probiotic strain(s) | $1 \times 10^9$ CFU |
|---|---|
| (b) Macrogol 4000 BP | 350 mg |

Capsules are prepared by melting the Macrogol 4000 BP, dispersing the probiotic strain(s) in the melt and filling the melt into a two-part hard gelatin capsule.

Formulation D (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

| (a) Probiotic strain(s) | $1 \times 10^9$ CFU |
|---|---|
| (b) Microcrystalline Cellulose | 125 mg |
| (c) Lactose BP | 125 mg |
| (d) Ethyl Cellulose | 13 mg |

Experimental Example 1

Materials and Methods

The possible anti-inflammatory activity of the probiotic product was evaluated in a randomized double-blind placebo-controlled trial with 66 healthy participants>70 years of age with low grade systemic inflammation (defined by C-reactive protein; serum level 2-10 mg/L).

Criteria for exclusion from the study were:

Intake of antibiotic treatment in the last four weeks before inclusion into the study;

Currently on corticosteroid treatment;

Presence of chronic inflammatory disease.

The subjects were randomly allocated to one of the three groups:

1. *Lactobacillus plantarum* Heal 9 (Lp Heal 9)

2. *Lactobacillus plantarum* Heal 9+berries (Bär+Lp Heal 9)

3. Placebo

Each study product was formulated as a powder at 10 g/dose and was to be mixed with sour milk/yoghurt and consumed once daily for a period of four weeks. Test Product A (for group 2) consisted of a daily dose of 1 billion colony forming units ($10^9$ CFU/dose) of freeze-dried *Lactobacillus plantarum* HEAL 9 probiotic bacteria, freeze dried berries (blackberries and blackcurrants) and maltodextrin. Test Product B (for group 1) consisted of a daily dose of 1 billion colony forming units ($10^9$ CFU/dose) of freeze-dried *Lactobacillus plantarum* HEAL 9 probiotic bacteria, and maltodextrin, treated to resemble Test Product A in appearance and taste. The placebo product consisted of maltodextrin, treated with colourants and flavourings/aromatic agents to resemble the Test Product A in appearance and taste.

The participants were also asked to keep a study diary throughout the study period for the documentation of their intestinal health and as a means for checking compliance and to refrain from taking other products containing probiotic bacteria.

Blood and faecal samples were taken at baseline and at the end of the study for the analysis of the following parameters:

1. Faecal samples were used for the analysis of calprotectin (a marker of gut inflammation) and zonulin (a protein that modulates the permeability of tight junctions between cells of the intestinal wall and is used as a marker of increased gut permeability);

2. Blood samples were used for the analysis of the systemic inflammation markers CRP and fibrinogen.

CRP levels in blood, serum and plasma may be determined using commercially available methods and apparatus, such as the Alere Afinion™ CRP assay using the Afinion™ AS100 analyser from Alere/Abbott (see www.alere.com).

This test is an in vitro method using a solid phase immunochemical assay based on a membrane coated with anti-human CRP antibodies, which react with CRP in the sample.

The analyser measures the colour intensity of the membrane, and this is proportional to the amount of CRP in the sample.

CRP levels in serum can be tested in a sensitive manner by a variety of methods (see Pearson T A et al (2003) Markers of inflammation and cardiovascular disease: application to clinical and public health practice: A statement for healthcare professionals from the Centers for Disease Control and Prevention and the American Heart Association. Circulation. 107; 499-511

Results

The Wilcoxon Rank-sum Test was used for statistical analysis in the study.

No differences in the levels of zonulin and fibrinogen were detected between the probiotic groups and the placebo.

However, the level of the inflammatory marker CRP increased over time in the placebo group (group 3) and reduced in the group receiving Lp HEAL 9 and berries—Bär+Lp Heal 9 (group 2) (FIG. 1). The effect was even more pronounced in the group consuming only probiotics, without the addition of berries (group 1) (FIG. 1).

The level of calprotectin expressed as mean change over time did not differ between either of the probiotic groups and placebo. However, there were significantly fewer participants in the *Lactobacillus plantarum* (Lp HEAL 9 only group (group 1) that showed increased levels for calprotectin over time compared to placebo (group 3) (p=0.028) (Table 1).

TABLE 1

Analysis of the number of participants with stable or reduced
levels of calprotectin vs increased levels of calprotectin

| | Participants with stable or reduced levels of calprotectin (% of group) | Participants with increased levels of calprotectin (% of group) | p-value |
|---|---|---|---|
| Group 1: Lp HEAL 9 | 15 (83.3) | 3 (16.6) | 0.028 |
| Group 3: Placebo | 11 (50) | 11 (50) | |

CONCLUSION

The results obtained with CRP and calprotectin show that *Lactobacillus plantarum*, in particular *Lactobacillus plantarum* HEAL 9, has efficacy in treating and/or preventing age-related systemic inflammation in otherwise healthy elderly people.

The invention claimed is:

1. A method for treating age-related systemic inflammation in a human in need thereof by reducing or preventing an increase in a level of serum C-reactive protein, the method comprising administering to the human at least one therapeutically effective dose of at least one probiotic strain of *Lactobacillus plantarum* deposited under accession number DSM 15312.

2. The method according to claim 1, wherein the human is aged more than 60, 65, 70, 75, 80, 85 or 90 years.

3. The method according to claim 1, wherein the human is a man.

4. The method according to claim 1, wherein the human is a woman.

5. The method according to claim 4, wherein the woman is a post-menopausal woman.

6. The method according to claim 1, wherein the effective dose of the at least one probiotic strain of *Lactobacillus plantarum* is administered at least once a day.

7. The method according to claim 1, wherein the effective dose of the at least one probiotic strain of *Lactobacillus plantarum* is from about $10^6$ to about $10^{14}$ colony forming units (CFU) per dose.

8. The method according to claim 1, wherein one or more effective doses of the at least one probiotic strain of *Lactobacillus plantarum* are administered in one day, and wherein the daily dose of the at least one probiotic strain of *Lactobacillus plantarum* is from about $10^6$ to about $10^{14}$ CFU per day.

9. The method according to claim 1, wherein the treatment of age-related systemic inflammation additionally reduces or prevents an increase in the level of calprotectin.

10. The method according to claim 1, wherein the at least one probiotic strain is administered in a composition comprising at least one carrier selected from the group consisting of a pharmaceutically acceptable carrier, a pharmaceutically acceptable excipient, a diluent, and a food.

11. The method according to claim 10, wherein the composition is provided in the form of a solution, suspension, emulsion, tablet, granule, powder, capsule, lozenge, chewing gum, or suppository.

12. The method according to claim 10, wherein the food is a cereal-based product, a dairy product, a juice drink, or a fermented food.

13. The method according to claim 1, wherein the human has systemic inflammation indicated by a serum C-reactive Protein level of 2-10 mg/L before treatment.

14. The method according to claim 1, wherein the human has systemic inflammation indicated by a serum C-reactive Protein level of 3-10 mg/L before treatment.

\* \* \* \* \*